(12) United States Patent
Gatto

(10) Patent No.: US 6,509,303 B1
(45) Date of Patent: Jan. 21, 2003

(54) OIL SOLUBLE MOLYBDENUM ADDITIVES FROM THE REACTION PRODUCT OF FATTY OILS AND MONOSUBSTITUTED ALKYLENE DIAMINES

(75) Inventor: Vincent James Gatto, Midlothian, VA (US)

(73) Assignee: Ethyl Corporation, Richmond, VA (US)

( * ) Notice: Subject to any disclaimer, the term of this patent is extended or adjusted under 35 U.S.C. 154(b) by 0 days.

(21) Appl. No.: 09/533,230

(22) Filed: Mar. 23, 2000

(51) Int. Cl.$^7$ .............................................. C10M 159/18
(52) U.S. Cl. ........................ 508/362; 508/367; 554/38; 556/57
(58) Field of Search ................................ 508/362, 367; 554/38; 556/57

(56) References Cited

U.S. PATENT DOCUMENTS

| 3,121,059 | A | | 2/1964 | De Young et al. |
|---|---|---|---|---|
| 4,164,473 | A | * | 8/1979 | Coupland et al. |
| 4,261,843 | A | * | 4/1981 | King et al. |
| 4,765,918 | A | | 8/1988 | Love et al. ................. 252/46.4 |
| 4,889,647 | A | * | 12/1989 | Rowan et al. |
| 5,137,647 | A | | 8/1992 | Karol ......................... 252/33.6 |
| 5,143,633 | A | * | 9/1992 | Gallo et al. |
| 6,103,674 | A | * | 8/2000 | Nalesnik et al. |

FOREIGN PATENT DOCUMENTS

| EP | 0 546357 A | 6/1993 |
|---|---|---|

* cited by examiner

*Primary Examiner*—Jerry D. Johnson
(74) *Attorney, Agent, or Firm*—Dennis H. Rainear

(57) ABSTRACT

Organic molybdenum complexes comprising the reaction products of fatty oils, a mono-alkylated alkylene diamine, and a molybdenum source and their use as multifunctional additives for lubricating compositions.

34 Claims, No Drawings

OIL SOLUBLE MOLYBDENUM ADDITIVES FROM THE REACTION PRODUCT OF FATTY OILS AND MONOSUBSTITUTED ALKYLENE DIAMINES

TECHNICAL FIELD

The present invention relates to novel organic molybdenum complexes and their use as multifunctional additives for lubricating compositions. The novel molybdenum compositions of the present invention comprise the reaction products of a fatty oil, a monoalkylated alkylene diamine and a molybdenum source.

BACKGROUND OF THE INVENTION

Lubricating oils for internal combustion engines of automobiles or trucks are subjected to a demanding environment during use. This environment results in the oil suffering oxidation that is catalyzed by the presence of impurities in the oil such as iron compounds and is also promoted by the elevated temperatures of the oil during use. This oxidation of lubricating oils during use is typically controlled to some extent by the use of antioxidant additives that may extend the useful life of the oil, particularly by reducing or preventing unacceptable viscosity increases.

Further, there have been many attempts to use lubricants to reduce the friction in an internal combustion engine so as to reduce the fuel consumption of the engine. Numerous classes of lubricant additives have been suggested for use as friction modifiers and to increase the energy efficiency provided to an engine by a lubricant.

Molybdenum containing additives are known to deliver a variety of beneficial properties to lubricants. Examples of lubricants that benefit from the addition of molybdenum are passenger car motor oils, natural gas engine oils, heavy-duty diesel oils, and railroad oils. Over the years molybdenum, when used properly, has been shown to deliver improved anti-wear protection, improved oxidation control, improved deposit control, and improved friction modification for fuel economy. There are many examples in the patent literature showing the use of molybdenum additives as antioxidants, deposit control additives, anti-wear additives and fiction modifiers. A partial list of molybdenum-containing lubricant patents is provided below:

| | | | |
|---|---|---|---|
| US 5,840,672 | US 5,814,587 | US 4,529,526 | WO 95/07966 |
| US 5,650,381 | US 4,812,246 | US 5,458,807 | WO 95/07964 |
| US 5,880,073 | US 5,658,862 | US 5,696,065 | WO 95/07963 |
| US 5,665,684 | US 4,360,438 | US 5,736,491 | WO 95/27022 |
| US 5,786,307 | US 4,501,678 | US 5,688,748 | EP 0 447 916 A1 |
| US 5,807,813 | US 4,692,256 | US 5,605,880 | WO 95/07962 |
| US 5,837,657 | US 4,832,867 | US 4,705,641 | EP 0 768 366 A1 |

Numerous oil-soluble molybdenum compounds and their methods of preparation have been described in the art. For example, glycol molybdate complexes are described by Price et al. in U.S. Pat. No. 3,285,942; overbased alkali metal and alkaline earth metal sulfonates, phenates and salicylate compositions containing molybdenum are disclosed and claimed by Hunt et al in U.S. Pat. No. 4,832,857; molybdenum complexes prepared by reacting a fatty oil, a diethanolamine and a molybdenum source are described by Rowan et al in U.S. Pat. No. 4,889,647; a sulfur and phosphorus-free organomolybdenum complex of organic amide, such as molybdenum containing compounds prepared from fatty acids and 2-(2-aminoethyl) aminoethanol are taught by Karol in U.S. Pat. No. 5,137,647; overbased molybdenum complexes prepared from arnines, diamines, alkoxylated amines, glycols and polyols are described by Gallo et al in U.S. Pat. No. 5,143,633; and 2,4-heteroatom substituted-molybdena-3,3-dioxacycloalkanes are described by Karol in U.S. Pat. No. 5,412,130.

Existing molybdenum technology, however, suffers from a number of problems that have limited its widespread use in lubricants. These problems include color, oil solubility, cost and corrosion.

Color—Many molybdenum technologies that appear in the patent literature deliver high levels of color when used even at moderate levels in crankcase oils. A non-discoloring molybdenum source is important because highly colored oils imply to the end consumer that the oil is "used" and therefore not capable of delivering the maximum amount of protection to the engine. When these highly colored molybdenum sources are used at low levels, e.g. 100–150 ppm delivered molybdenum as is typically required for oxidation, deposit and wear control, discoloration is not substantial but may still be visible. However, when these highly colored molybdenum compounds are used at high levels, e.g. 400–1000 ppm delivered molybdenum as is generally required for friction modification, discoloration is often significant. Traditionally, the color of fully formulated crankcase oils has been determined using the ASTM D 1500 color scale. Two types of unacceptable colors are possible. The first type of discoloration results in a dark rating on the D 1500 scale. The amount of acceptable finished lubricant darkening depends on the customer and application. There are no set standards for the amount of discoloration or darkening that is allowed. Generally, D 1500 ratings equal to or greater than 5.0 are considered unacceptable for a finished crankcase oil. Certain customers may find it difficult to market and sell such dark crankcase oils. The second type of discoloration produces "no match" on the D 1500 color scale. These finished lubricants, in addition to showing no match, are also very dark. Again, certain customers may find it difficult to market and sell such dark crankcase oils.

Oil Solubility—Many commercially available molybdenum additives designed for use in lubricants exhibit limited solubility in the finished lubricant product. For widespread use of a molybdenum product in lubricant applications the product must not only be soluble, at friction modifier treat levels, in the finished lubricant, it must also be soluble in the additive concentrates used to prepare the finished lubricant.

Cost—Molybdenum has long been viewed as an expensive additive for crankcase applications. Part of the reason for the high cost stems from the fact that many of the commercial molybdenum products have low levels, e.g. less than 5% by weight, of molybdenum in the additive. In some cases expensive organic ligands or expensive manufacturing processes are used to produce the commercial molybdenum compounds. There is a need for products with higher molybdenum contents that are prepared from lower cost raw materials.

Corrosion—Many molybdenum technologies that appear in the patent literature contain sulfur. The presence of sulfur in certain crankcase applications is detrimental because certain types of sulfur are incompatible with elastomer seals and corrosive. Even the less aggressive forms of sulfur can be corrosive in very high temperature crankcase environments where significant amounts of oxygen and water are present. There are also trends to reduce the amount of sulfur present in finished crankcase lubricants. As these trends start to become a reality additives containing sulfur will become less desirable.

All the above problems suggest a need for a molybdenum additive that has a high molybdenum content, good oil solubility, non-discoloring to base oil and finished crankcase oils, and free of sulfur. It has unexpectedly been found that the molybdenum additives of the present invention provide the above benefits to lubricating compositions without the attendant problems commonly associated with molybdenum additives.

SUMMARY OF THE INVENTION

In one aspect, this invention is directed to molybdenum compositions that show excellent oil solubility and a low tendency to color finished crankcase oils. These molybdenum additives comprise the reaction products of fatty oils, mono-alkylated alkylene diamines and a molybdenum source.

In another embodiment, the present invention is directed to methods for improving the antioxidancy and friction properties of a lubricant by incorporating into the lubricant the novel molybdenum additives of the present invention.

DETAILED DESCRIPTION OF THE INVENTION

The molybdenum complexes of the present invention comprise the reaction products of fatty oils, mono-alkylated alkylene diamines and a molybdenum source.

A suitable reaction to prepare these molybdenum additives is basically a two step process. The first step involves preparing an aminoamide/glyceride mixture. This mixture is prepared by reacting a fatty oil with a mono-substituted alkylene diamine at an elevated temperature. The second step involves carrying out the molybdenum incorporation.

The fatty oil—There are two requirements for the fatty oil. First, the fatty oil must be capable of reacting with the mono-substituted alkylene diamine to form the aminoamide/glyceride mixture. Second, the mixture thus formed must be able to react with at least one equivalent of molybdenum based on the amount of fatty oil used. Examples of fatty oils that may be used include cottonseed oil, groundnut oil, coconut oil, linseed oil, palm kernel oil, olive oil, corn oil, palm oil, caster oil, rapeseed oil (low or high erucic acids), soyabean oil, sunflower oil, herring oil, sardine oil, and tallow. These fatty oils are generally known as glyceryl esters of fatty acids, triacylglycerols or triglycerides and have the chemical structure shown below:

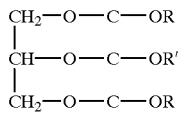

where R, R' and R" are independently saturated or unsaturated aliphatic hydrocarbons having from 3 to 23 carbon atoms. The preferred hydrocarbon chains have 12 to 24 carbon atoms (i.e., R, R' and R"=11 to 23), but this can vary based on the diamine used. Often, the triglycerides are described in terms of the fatty acids that make up the triglycerides. For example, approximately 48% by weight of the fatty acids that make up coconut oil are $C_{12}$ saturated acids (lauric acid), while canola oil has a fatty acid composition of approximately 90% by weight of $C_{18}$ saturated and unsaturated hydrocarbons.

The diamine—The limitations of the diamine are similar to those of the fatty oil. First, the amine must be capable of reacting with the fatty oil. Second, the intermediate aminoamide/glyceride mixture must be able to react with the molybdenum source. In addition, the diamine must be mono-alkylated. Examples of some mono-alkylated alkylene diamines that may be used include methylaminopropylamine, methylaminoethylamine, butylaminopropylamine, butylaminoethylamine, octylaminopropylamine, octylaminoethylamine, dodecylaaminopropylaamine, dodecylaminoethylamine, hexadecylaminopropylamine, hexadecylaminoethylamine, octadecylaminopropylamine, octadecylaminoethylamine, isopropyloxypropyl-1,3-diaminopropane, and octyloxypropyl-1,3-diaminopropane. Mono-alkylated alkylene diamines derived from fatty acids may also be used. Examples include N-coco alkyl-1,3-propanediamine (Duomeen™ C), N-tall oil alkyl-1,3-propanediamine (Duomeen™ T) and N-oleyl-1,3-propanediamine (Duomeen™ O), all commercially available from Akzo Nobel.

The amount of diamine used can vary and is based on the type of fatty oil used. The molar ratio of diamine to fatty oil can vary from 1:1 to 3:1. The preferred ratio is 2:1.

The reaction between the fatty oil and mono-alkylated alkylene diamine is typically carried out between 75 and 150° C. by combining the two materials and heating with mixing and under a nitrogen atmosphere. The preferred reaction temperature is between 100 and 120° C. Reaction times may vary, and typically range from 1 hour to 4 hours. A reaction solvent may be used as long as it does not react with the fatty oil or diamine. Preferred reaction solvents include toluene, xylenes, heptane, and various naphthenic, paraffinic and synthetic diluent oils. The amount of solvent used is not critical but is kept to a minimum for practical purposes.

Molybdenum Incorporation—The source of molybdenum is an oxygen-containing molybdenum compound capable of reacting with the reaction product of the fatty oil and the mono-substituted diamine. The sources of molybdenum include, among others, ammonium molybdates, sodium molybdate, molybdenum oxides and mixtures thereof. A particularly preferred molybdenum source comprises molybdenum trioxide.

The addition of water to these reactions is not required, however, water can facilitate the reaction rate and significantly improve the yields based on molybdenum incorporation. Water should be removed to drive the reaction to completion and maximize the amount of molybdenum incorporated.

An example of a suitable method of molybdenum incorporation is as follows: molybdenum trioxide and water are added to the aminoamide/glyceride reaction mass maintained at approximately 60–80° C. The molar ratio of molybdenum trioxide to fatty oil can vary from 1:1 to 2:1. Water is typically added in an amount equivalent to the amount of molybdenum trioxide used, but higher levels of water may be used. After addition of the molybdenum trioxide and water the reaction is slowly heated to reflux temperature with gradual removal of water. Water may be removed by distillation, vacuum distillation, or by azeotropic distillation from a suitable solvent. Suitable solvents include toluene, xylenes, and heptane. The reaction can be monitored by removal of water. The amount of water collected is equal to the amount added plus the amount generated to produce the aminoamide/glyceride molybdenum complex. For example, if 14.4 g of molybdenum trioxide are used with 14.4 g of water, the amount of water collected will be 14.4+14.4/143.94*18.01=16.2, where 143.94 is the molecular weight of molybdenum trioxide and 18.01 is the molecular weight of the water generated in the reaction. The reaction generally requires 1 to 10 hours. At the end of the reaction period the mixture is cooled, filtered to remove any unreacted molybdenum trioxide and, if used, the solvent removed by vacuum distillation. In many cases filtration is not required because all of the molybdenum trioxide is reacted. From a practical and cost standpoint, it is desirable to react all of the molybdenum trioxide. The product prepared by this process is a dark amber wax or viscous liquid.

In a preferred embodiment, the aminoamide/glyceride mixture is prepared by reacting a mono-alkylated alkylene diamine with a fatty oil, wherein the fatty oil is derived predominantly from $C_{14}$ or lower fatty acids, e.g., coconut oil, wherein at least 50% of the fatty acids that make up the fatty oil are saturated and/or unsaturated fatty acids having 14 carbon atoms or less.

In another preferred embodiment, the aminoamide/glyceride mixture is prepared by reacting methylaminopropylamine with a fatty oil, wherein the fatty oil is derived predominantly from $C_{16}$ or higher fatty acids (for example, canola oil, cottonseed oil, groundnut oil, linseed oil, olive oil, corn oil, palm oil, rapeseed oil, soybean oil, sunflower oil and tallow oil) wherein at least 50% of the fatty acids that make up the fatty oil are saturated and/or unsaturated fatty acids having at least 16 carbon atoms.

The molybdenum complexes of the present invention are oil-soluble molybdenum compounds substantially free of reactive sulfur. As used herein the term "oil-soluble molybdenum compound substantially free of reactive sulfur" means any molybdenum compound that is soluble in the lubricant or formulated lubricant package and is substantially free of reactive sulfur. The term reactive sulfur is sometimes referred to as divalent sulfur or oxidizable sulfur. Reactive sulfur also includes free sulfur, labile sulfur or elemental sulfur, all of which are sometimes referred to as "active" sulfur. Active sulfur is sometimes referred to in terms of the detrimental effects it produces. These detrimental effects include corrosion and elastomer seal incompatibility. As a result, "active" sulfur is also referred to as "corrosive sulfur" or "seal incompatible sulfur". The forms of reactive sulfur that contain free, or "active" sulfur, are much more corrosive to engine parts than reactive sulfur that is very low in free or "active" sulfur. At high temperatures and under severe conditions, even the less corrosive forms of reactive sulfur can cause corrosion. It is therefore desirable to have a molybdenum compound that is substantially free of all reactive sulfur, active or less active. By "soluble" or "oil-soluble" it is meant that the molybdenum compound is oil-soluble or capable of being solubilized under normal blending or use conditions into the lubrication oil or diluent for the concentrate. By "substantially free" it is meant that trace levels of sulfur may be present due to impurities or catalysts left behind from the manufacturing process. This sulfur is not part of the molybdenum compound itself, but is left behind from the preparation of the molybdenum compound. Such impurities can sometimes deliver as much as 0.05 weight percent of sulfur to the final molybdenum product.

The molybdenum additives of the present invention may be used as antioxidants, deposit control additives, anti-wear additives and/or friction modifiers. The treat rates of the molybdenum additives depend upon the desired finished lubricant properties, however, typically the additives are present in an amount so as to provide at least about 50, and preferably from about 50 to about 1000 ppm, of molybdenum to the finished lubricant. The concentration of molybdenum in the lubricants according to the invention has no particular upper limit, however, for economic reasons a maximum level of about 1000 ppm is generally preferred although not required.

The molybdenum complexes of the present invention have excellent solubility in a wide variety of basestock types and have a reduced tendency to color finished crankcase oils. Further, the complexes have high molybdenum incorporations, may be prepared from low cost raw materials and have straightforward production processes. In a preferred embodiment, the molybdenum complexes of the invention, undiluted, contain greater than 7 weight percent of molybdenum.

The composition of the lubricant oil can vary significantly based on the customer and specific application. The oil will typically contain, in addition to the molybdenum compounds of the invention, a detergent/inhibitor additive package and a viscosity index improver. In general, the lubricant oil is a formulated oil which is composed of between 65 and 95 weight percent (wt. %) of a base oil of lubricating viscosity, between 0 and 30 wt. % of a polymeric viscosity index improver, between about 5 and 15 wt. % of an additional additive package and typically a sufficient amount of molybdenum complex to provide at least about 50 ppm of molybdenum to the finished lubricant.

The detergent/inhibitor additive package may include dispersants, detergents, zinc dihydrocarbyl dithiophosphates (ZDDP), additional antioxidants, corrosion inhibitors, rust inhibitors, foam inhibitors and supplemental friction modifiers.

The dispersants are nonmetallic additives containing nitrogen or oxygen polar groups attached to a high molecular weight hydrocarbon chain. The hydrocarbon chain provides solubility in the hydrocarbon base stocks. The dispersant functions to keep oil degradation products suspended in the oil. Examples of commonly used dispersants include hydrocarbyl-substituted succinimides, hydrocarbyl amines, polyhydroxy succinic esters, hydrocarbyl-substituted Mannich bases, and hydrocarbyl-substituted triazoles. Generally, the dispersant is present in the finished oil in an amount between 0 and 10 wt. %.

The detergents are metallic additives containing charged polar groups, such as phenates, sulfonates or carboxylates, with aliphatic, cycloaliphatic, or alkylaromatic chains, and several metal ions. The detergents function by lifting deposits from the various surfaces of the engine. Examples of commonly used detergents include neutral and overbased alkali and alkaline earth metal sulfonates, overbased alkaline earth salicylates, phosphonates, thiopyrophosphonates, and thiophosphonates. Generally, when used, the detergents are present in the finished oil in an amount from about 0.5 and 5.0 wt. %.

The ZDDP's are the most commonly used antiwear additives in formulated lubricants. These additives function by reacting with the metal surface to form a new surface active compound which itself is deformed and thus protects the original engine surface. Other examples of anti-wear additives include tricresol phosphate, dilauryl phosphate, sulfurrized terpenes and sulfurized fats. The ZDDP also functions as an antioxidant. Generally, the ZDDP is present in the finished oil between about 0.25 and 1.5 wt. %. It is desirable from environmental concerns to have lower levels of ZDDP. Phosphorus-free oils contain no ZDDP.

The inclusion of the present molybdenum compounds generally removes the need for supplementary antioxidants. However, a supplementary antioxidant may be included in oils that are less oxidatively stable or in oils that are subjected to unusually severe conditions. The amount of supplemental antioxidant will vary depending on the oxidative stability of the base stock. Typical treat levels in finished oils can vary from 0 to 2.5 wt %. The supplementary antioxidants that are generally used include diarylamines, hindered phenols, hindered bisphenols, sulfurized phenols, sulfurized olefins, alkyl sulfides and polysulfides, dialkyl dithiocarbamates, and phenothiazines.

The base oil according to the present invention may be selected from any of the synthetic or natural oils or mixtures thereof. These oils are typical crankcase lubrication oils for spark-ignited and compression-ignited internal combustion engines, for example natural gas engines, automobile and truck engines, marine, and railroad diesel engines. The synthetic base oils include alkyl esters of dicarboxylic acids, polyglycols and alcohols, poly-alpha-olefins, including polybutenes, alkyl benzenes, organic esters of phosphoric acids, and polysilicone oils. Natural base oils include mineral lubrication oils that may vary widely as to their crude source, e.g., as to whether they are paraffinic, naphthenic, or mixed paraffinic-naphthenic. The base oil typically has a viscosity of about 2 to about 15 cSt and preferably about 2.5 to about 11 cSt at 100° C.

The lubricating oil compositions of this invention can be made by adding the molybdenum compound, and any supplemental additives, to an oil of lubricating viscosity. The method or order of component addition is not critical. Alternatively, the molybdenum compounds, along with any additional additives, can be added to the oil as a concentrate.

The lubricating oil concentrate will typically comprise a solvent and from about 2.5 to 90 wt. % and preferably 5 to 75 wt. % of the combination of the molybdenum compound of this invention and the optional supplemental additives. Preferably the concentrate comprises at least 25 wt. % and most preferably at least 50 wt. % of the combination of molybdenum compound and supplemental additives.

In one embodiment, the present invention is directed to a method of improving the oxidation stability of a lubricating oil, wherein said method comprises adding to a lubricating oil an oxidation stability improving amount of the molybdenum complexes of the present invention, wherein said oxidation stability improving amount of said molybdenum complex is effective to improve the oxidative stability of the lubricating oil, as compared to the same lubricating oil except that it is devoid of said molybdenum complex. For improving the oxidation stability of the oil, the molybdenum complex is typically present in the lubricating oil in an amount sufficient to provide at least 50 ppm, preferably at least 100 ppm and more preferably at least 150 ppm, of molybdenum to the finished lubricating oil.

In one embodiment, the present invention is directed to a method of improving the fuel economy of an internal combustion engine, wherein said method comprises using as the crankcase lubricating oil for said internal combustion engine a lubricating oil containing the molybdenum complexes of the present invention, wherein said molybdenum complex is present in an amount sufficient to improve the fuel economy of the internal combustion engine using said crankcase lubricating oil, as compared to said engine operated in the same manner and using the same crankcase lubricating oil except that the oil is devoid of said molybdenum complex. For improving fuel economy, the molybdenum complex is typically present in the lubricating oil in an amount sufficient to provide at least 150 ppm, preferably at least 400 ppm and more preferably at least 800 ppm, of molybdenum to the finished lubricating oil.

In one embodiment, the present invention is directed to a method of reducing deposits in an internal combustion engine, wherein said method comprises using as the crankcase lubricating oil for said internal combustion engine a lubricating oil containing the molybdenum complexes of the present invention, wherein said molybdenum complex is present in an amount sufficient to reduce the weight of deposits in an internal combustion engine operated using said crankcase lubricating oil, as compared to the weight of deposits in said engine operated in the same manner and using the same crankcase lubricating oil except that the oil is devoid of said molybdenum complex. For reducing deposits, the molybdenum complex is typically present in the lubricating oil in an amount sufficient to provide at least 50 ppm, preferably at least 100 ppm and more preferably at least 150 ppm, of molybdenum to the finished lubricating oil. Representative of the deposits that may be reduced using the compositions of the present invention include piston deposits, ring land deposits, crown land deposits and top land deposits.

In one embodiment, the present invention is directed to a method of reducing wear in an internal combustion engine, wherein said method comprises using as the crankcase lubricating oil for said internal combustion engine a lubricating oil containing the molybdenum complexes of the present invention, wherein said molybdenum complex is present in an amount sufficient to reduce the wear in an internal combustion engine operated using said crankcase lubricating oil, as compared to the wear in said engine operated in the same manner and using the same crankcase lubricating oil except that the oil is devoid of said molybdenum complex. For reducing wear, the molybdenum complex is typically present in the lubricating oil in an amount sufficient to provide at least 50 ppm, preferably at least 100 ppm and more preferably at least 150 ppm, of molybdenum to the finished lubricating oil. Representative of the types of wear that may be reduced using the compositions of the present invention include cam wear and lifter wear.

The following examples are illustrative of the invention and its advantageous properties and are not intended to be limiting. In these examples as well as elsewhere in this application, all parts and percentages are by weight unless otherwise indicated.

EXAMPLES

The general synthetic method for preparation of the molybdenum compounds in the following Examples involves first preparing a glyceride/aminoamide mixture as follows: A four-neck reaction flask is equipped with a stirrer, a thermometer, a reflux condenser, and a nitrogen inlet. The flask is charged with the mono-substituted alkylene amine and fatty oil. Dry nitrogen is passed into the reactor through the inlet and out of the reactor through the reflux condenser. The reaction is stirred, heated to about 120° C. and maintained at that temperature for 2 to 3 hours. The reaction is then cooled to about 75° C. and prepared for the molybdenum incorporation step.

In the molybdenum incorporation step, toluene or xylenes is added to help with the removal of water. A dean-stark trap is placed between the reaction flask and the reflux condenser. The reaction solvent is added to the reactor and additional solvent is used to fill the dean-stark trap. The reaction is maintained at 75–80° C. while the molybdic oxide and water is added. The reaction mixture is mixed vigorously and brought to reflux temperature. Water is removed from the reaction via the dean-stark trap. The reaction mixture is then cooled and filtered through a pre-weighed filter pad. The filtrate is concentrated on a rotary evaporator until all the solvent is removed. The amount of unreacted molybdenum is determined from the weight gain of the filter pad after filtration. Sample M.1 was diluted with a paraffinic process diluent oil to contain 70 wt. % of the molybdenum compound. All other samples were not diluted.

Table 1 sets forth various reaction products in terms of the fatty oil and the amine used as well as the amount of incorporated molybdenum (percent molybdenum based on the weight of the complex). In the preparations of samples M.1 through M.5, the molybdenum source was molybdenum trioxide and the components were reacted together in a molar ratio of fatty oil:amine:molybdenum compound of 1:2:1. For sample M.6, the molar ratio of fatty oil:amine:molybdenum compound was 1:1:1. For sample M.7, the molar ratio of fatty oil:amine:molybdenum compound was 2:2:1. The amines used in M.6 and M.7 are taught in the prior art as useful amines for preparing molybdenum complexes. The amine used in M.6 is taught in U.S. Pat. No. 5,137,647 while the amine used in M.7 is taught in U.S. Pat. No. 4,765,918. The amines of M.6 and M.7 are not mono-alkylated alkylene diamine and are therefore outside the scope of the present invention.

TABLE 1

| Sample | Fatty Oil | Amine Type | % Molybdenum |
|---|---|---|---|
| M.1 (#149) | Coconut Oil | Duomeen ™ C | 5.63 |
| M.2 (#158) | Coconut Oil | Duomeen ™ O | 6.91 |
| M.3 (#101) | Canola Oil | Methylaminopropylamine | 8.31 |
| M.4 (#113) | Coconut Oil | Methylaminopropylamine | 9.15 |
| M.5 (#105) | Coconut Oil | Duomeen ™ C | 7.15 |
| M.6 (#109)* | Canola Oil | 2-(2-Aminoethylamino)ethanol | 6.60 |
| M.7 (#111)* | Coconut Oil | Diethylenetriamine | 5.51 |

*Comparative Examples

The color and a visual solubility check was determined for the molybdenum compounds using a fully-formulated 5W-30 passenger car motor oil (PCMO) as well as a paraffinic process oil diluent (PO#5). The color method was ASTM D1500. Color results are reported to the nearest one-half unit match on the D1500 color scale. The treat levels in Table 2 are based on the amount (weight percent) of molybdenum compound added to the oil, not the amount of molybdenum delivered to the oil.

TABLE 2

| | Aesthetic Properties | | | | |
|---|---|---|---|---|---|
| Molybdenum type | Solubility in PO #5 | Color in PO #5 (1 wt. % treat) | Solubility in PCMO | Color in PCMO (1 wt. % treat) | Color in PCMO (0.5 wt. % treat) |
| M.1 | Hazy | 1.0 | Soluble | 3.0 | 3.0 |
| M.2 | Soluble | 1.0 | Soluble | 3.5 | 3.0 |
| M.3 | Soluble | 1.5 | Soluble | 4.0 | 3.5 |
| M.4 | Insoluble | Not Tested | Soluble | 4.0 | 3.5 |
| M.5 | Soluble | 1.5 | Soluble | 3.5 | 3.0 |
| M.6* | Soluble | 3.5 | Soluble | 5.5 | 4.5 |
| M.7* | Hazy | 4.0 | Soluble | No Match | 4.5 |

*Comparative Examples

It is clear, from an examination of Table 2, that the molybdenum compounds of the present invention (M.1 to M.5) all gave exceptionally low colors at friction modifier treat levels in finished PCMO. It is also clear that the type of amine used to prepare the oil soluble molybdenum compound is critical for producing a product that delivers low color to process oil and finished PCMO. The amine used in M.6, 2-(2-aminoethylamino)ethanol, and the amine used in M.7, produced products that contributed substantial color in process oil and PCMO versus that seen with the molybdenum compounds M.1 through M.5 of this invention.

The antioxidant performance of the molybdenum additives in a 5W-30 PCMO was determined using pressurized differential scanning calorimetry (PDSC). Test oils were prepared by adding the molybdenum additives, as described in Table 1, to a pre-blend oil. The pre-blend oil was similar to a commercially available PCMO formulation used in 5W-30 passenger car motor oils.

The PDSC procedure used is described by J. A. Walker and W. Tsang in "Characterization of Lubrication Oils by Differential Scanning Calorimetry", SAE Technical Paper Series, 801383 (Oct. 20–23, 1980). Oil samples were treated with an iron naphthenate catalyst (50 ppm Fe) and approximately 2 milligrams were analyzed in an open aluminum hermetic pan. The DSC cell was pressurized with 400 psi of air containing approximately 55 ppm $NO_2$ as an oxidation catalyst. The temperature ramping method was used wherein the temperature is ramped at 2.5° C. per minute up to 250° C. During the temperature ramping sequence an exothermic release of heat is observed. This exothermic release of heat marks the oxidation reaction. The temperature at which the exothermic release of heat is observed is called the oxidation onset temperature and is a measure of the oxidative stability of the oil (i.e., the higher the oxidation onset temperature the greater the oxidative stability of the oil). All oils were evaluated in multiple runs and the results averaged. The results are set forth in Table 3.

TABLE 3

PDSC Results

| Oil # | Molybdenum type | Amount of molybdenum in the finished oil (ppm Mo) | Onset Temperature (° C.) |
|---|---|---|---|
| 1* | — | 0 | 206.9 |
| 2 | M.1 | 150 | 215.1 |
| 3 | M.1 | 400 | 216.5 |
| 4 | M.1 | 600 | 214.5 |
| 5 | M.2 | 150 | 218.2 |
| 6 | M.2 | 400 | 219.2 |
| 7 | M.2 | 600 | 219.7 |
| 8 | M.3 | 150 | 216.5 |
| 9 | M.3 | 400 | 216.6 |
| 10 | M.3 | 600 | 217.6 |
| 11 | M.5 | 150 | 217.2 |
| 12 | M.5 | 400 | 218.3 |
| 13 | M.5 | 600 | 220.3 |

*Comparative results

The onset temperature results in Table 3 clearly show the efficacy of the molybdenum compounds according to the invention (Oils #2–13) in controlling oxidation in fully formulated passenger car motor oils.

The deposit control performance of the molybdenum additives in a 5W-30 PCMO was determined using a modified version of the Caterpillar Micro-Oxidation Test (CMOT) as reported by Fulvio Zerla and Robert Moore in "Evaluation of Diesel Engine Lubricants by Micro-Oxidation" SAE Technical Paper 890239 (1989). The CMOT is a comumonly used technique for evaluating the deposit forming tendencies of a wide variety of passenger car and diesel lubricants as well as mineral and synthetic basestocks. The test measures the oxidative stability and deposit forming tendencies of lubricants under high temperature thin-film oxidation conditions. The ability to easily vary test conditions and the flexibility of presenting test results makes it a valuable research tool for screening a wide variety of lubricant products.

In the CMOT, a thin-film of oil is placed in a weighed indented low carbon steel sample holder immersed in a test tube that is placed in a high temperature bath. Dry air is passed, at a specific rate, through the test tube, over the oil sample, and out of the test tube to the atmosphere. At specific time intervals the carbon steel sample holders are removed from the high temperature bath, rinsed with solvent to remove any remaining oil, and oven dried. The sample holders are weighed to determine the amount of deposit formed at the sampling interval. The method requires sampling at a variety of time intervals and determining percent deposits at each time interval. The CMOT tests were run using a temperature of 220° C., an air flow of 20 cc/min and sampling times of 90, 120, 150 and 180 minutes. All of the molybdenum compounds were present in the oils so as to provide 150 ppm of molybdenum to the finished lubricant.

The % Deposits at different sampling times are set forth in Table 4.

TABLE 4

CMOT Results

| Oil # | Molybdenum type | 90 Min. | 120 Min. | 150 Min. | 180 Min. |
|---|---|---|---|---|---|
| 1* | None | 22.7 | 26.0 | 28.6 | 26.4 |
| 2 | M.1 | 1.1 | 13.8 | 22.9 | 24.3 |
| 3 | M.2 | 0.8 | 1.8 | 9.9 | 22.5 |
| 4 | M.3 | 1.3 | 3.8 | 16.8 | 16.7 |
| 5 | M.5 | 2.6 | 14.7 | 23.5 | 19.7 |

*Comparative Examples

The results presented in Table 4 clearly indicate that the additive components according to the invention (Oils #2–5) provide improved deposit control in the CMOT as evidenced by the lower amount of deposit formation compared to the molybdenum-free lubricant.

Boundary lubrication occurs when fluid films are thin enough that opposing metal surfaces interact with one another. When this interaction occurs, friction increases. In an engine, an increase in friction results in a decrease in fuel economy.

The boundary friction coefficient of the molybdenum additives in a 5W-30 PCMO was determined using a High Frequency Reciprocating Rig (HFRR). The HFRR operates by oscillating a ball across a plate in a sample cell containing 1–2 ml of sample. The frequency of oscillation, path length that the ball travels, load applied to the ball and test temperature can be controlled. By controlling these parameters, the boundary frictional properties of a fluid can be assessed.

The novel molybdenum additives of the present invention were blended into SAE 5W-30 fully formulated motor oils. The boundary frictional properties of these fluids were assessed using an HFRR under conditions similar to those described by C. Bovington, V. Anghel and H. A. Spikes, in "Predicting Seq. VI and VIA Fuel Economy from Laboratory Bench Tests" (SAE Technical Paper 961142), that is, 4N load, 1 mm path length, 20 Hz frequency. The frictional properties were measured at 130° C.

Table 5 demonstrates the improvements in boundary friction results obtained by the addition of the novel molybdenum additives of the present invention to motor oils as compared to motor oils containing no molybdenum. Lower boundary friction results are indicative of improved fuel economy.

TABLE 5

Boundary Friction Results

| Oil # | Molybdenum type | Amount of molybdenum in the finished oil (ppm Mo) | Boundary Friction Coefficient |
|---|---|---|---|
| 1* | None | 0 | 0.087 |
| 2 | M.1 | 600 | 0.054 |
| 3 | M.2 | 800 | 0.075 |
| 4 | M.5 | 800 | 0.078 |

*Comparative examples

It is clear from Table 5 that oils containing the molybdenum additives of the present invention (Oils #2–4) exhibit improved (i.e., reduced) boundary friction, which is indicative of improved fuel economy as described above, compared to the molybdenum-free lubricating oil.

This invention is susceptible to considerable variation in its practice. Accordingly, this invention is not limited to the specific exemplifications set forth hereinabove. Rather, this invention is within the spirit and scope of the appended claims, including the equivalents available as a matter of law.

The patentee does not intend to dedicate any disclosed embodiments to the public, and to the extent any disclosed modifications or alterations may not literally fall within the scope of the claims, they are considered to be part of the invention under the doctrine of equivalents.

What is claimed is:

1. An organic molybdenum complex comprising the reaction product produced by combining for a sufficient time and temperature:
   i) at least one fatty oil;
   ii) at least one mono-alkylated alkylene diamine;
   iii) an oxygen-containing molybdenum source; and
   iv) water as a promoter, wherein the reaction product contains less than 0.05 weight percent of sulfur and the molybdenum content in the final reaction product is from 8.31 to 16.3 weight percent.

2. The molybdenum complex of claim 1 wherein said fatty oil comprises $C_{12}$ fatty acids as the predominant fatty acid component.

3. The molybdenum complex of claim 2 wherein said fatty oil comprises coconut oil.

4. The molybdenum complex of claim 1 wherein said fatty oil comprises $C_{18}$ fatty acids as the predominant fatty acid component.

5. The molybdenum complex of claim 4 wherein said fatty oil comprises canola oil.

6. The molybdenum complex of claim 4 wherein said mono-alkylated alkylene diamine comprises methylaminopropylamine.

7. The molybdenum complex of claim 1 wherein said mono-alkylated alkylene diamine comprises at least one member selected from the group consisting of methylaminopropylamine, methylaminoethylamine, butylaminopropylamine, butylaminoethylamine, octylammopropylamine, octylaminoethylamine, dodecylaminopropylamine, dodecylaminoethyrlamine, hexadecylaminopropylamine, hexadecylaminoethylamine, octadecylaminopropylamine, octadecylaminoethylamine, isopropyloxypropyl-1,3-diaminopropane, octyloxypropyl-1,3-diaminopropane and mono-alkylated alkylene diamines derived from fatty acids.

8. The molybdenum complex of claim 7 wherein said mono-alkylated alkylene diamine comprises at least one member selected from the group consisting of N-coco alkyl-1,3-propanediamine, N-tallow alkyl-1,3-propanediamine and N-oleyl-1,3-propanediamine.

9. The molybdenum complex of claim 1 wherein the molybdenum source comprises at least one member selected from the group consisting of ammonium molybdate, sodium molybdate and molybdenum oxides.

10. The molybdenum complex of claim 1 obtained by reacting (i) and (ii) at temperatures between 75 and 150° C. to form an intermediate reaction product prior to the addition of components (iii) and (iv).

11. The molybdenum complex of claim 10 wherein the intermediate reaction product comprises an aminoamide/glyceride mixture.

12. The molybdenum complex of claim 1 wherein the reaction product is substantially free of reactive sulfur.

13. A lubricating oil composition comprising a major amount of an oil of lubricating viscosity and the molybdenum complex of claim 1.

14. The lubricating oil composition of claim 13 wherein the molybdenum complex is present in an amount sufficient to provide at least about 50 ppm of molybdenum to the finished lubricant.

15. A method of improving the fuel economy of an internal combustion engine comprising lubricating said internal combustion engine with the lubricating oil of claim 13, wherein said molybdenum complex is present in an amount sufficient to improve the fuel economy of the internal combustion engine lubricated with said lubricating oil, as compared to said engine operated in the same manner and lubricated with the same lubricating oil except that the oil is devoid of said molybdenum complex.

16. The method of claim 15 wherein the molybdenum complex is present in said crankcase lubricating oil in an amount sufficient to provide at least 200 ppm of molybdenum to the finished lubricating oil.

17. A method of reducing deposits in an internal combustion engine comprising lubricating said internal combustion engine with the lubricating oil of claim 13, wherein said molybdenum complex is present in an amount sufficient to reduce the weight of deposits in said internal combustion engine lubricated with said crankcase lubricating oil, as compared to the weight of deposits in said engine operated in the same manner and lubricated with the same lubricating oil except that the oil is devoid of said molybdenum complex.

18. The method of claim 17 wherein the molybdenum complex is present in said crankcase lubricating oil in an amount sufficient to provide at least 50 ppm of molybdenum to the finished lubricating oil.

19. A method of reducing wear in an internal combustion engine comprising lubricating said internal combustion engine with the lubricating oil of claim 13, wherein said molybdenum complex is present in an amount sufficient to reduce the wear in said internal combustion engine lubricated with said lubricating oil, as compared to the wear in said engine operated in the same manner and lubricated with the same lubricating oil except that the oil is devoid of said molybdenum complex.

20. The method of claim 19 wherein the molybdenum complex is present in said crankcase lubricating oil in an amount sufficient to provide at least 50 ppm of molybdenum to the finished lubricating oil.

21. A method of improving the oxidation stability of a lubricating oil comprising adding to said lubricating oil an oxidation stability improving amount of the molybdenum complex of claim 1, wherein said oxidation stability improving amount of said molybdenum complex is sufficient to improve the oxidative stability of the lubricating oil, as compared to the same lubricating oil except that it is devoid of said molybdenum complex.

22. The method of claim 21 wherein the molybdenum complex is present in the lubricating oil in an amount sufficient to provide at least 50 ppm of molybdenum to the finished lubricating oil.

23. A process for preparing an organic molybdenum complex, said process comprises reacting for a sufficient time and temperature:
  i) at least one fatty oil;
  ii) at least one mono-alkylated alkylene diamine;
  iii) an oxygen-containing molybdenum source; and
  iv) water as a promoter, wherein the reaction product contains less than 0.05 weight percent of sulfur and the molybdenum content in the final reaction product is greater than 7.0 weight percent.

24. The process of claim 23, wherein said fatty oil comprises $C_{12}$ fatty acids as the predominant fatty acid component.

25. The process of claim 24, wherein said fatty oil comprises coconut oil.

26. The process of claim 23, wherein said fatty oil comprises $C_{18}$ fatty acids as the predominant fatty acid component.

27. The process of claim 26, wherein said fatty oil comprises canola oil.

28. The process of claim 26, wherein said mono-allylated alkylene diamine comprises methylaminopropylamine.

29. The process of claim 23, wherein the mono-alkylated alkylene diamine (component ii) is present in an amount of from 1 to 2 moles per mole of fatty oil (component i).

30. The process of claim 23, wherein said mono-alkylated alkylene diamine comprises at least one member selected from the group consisting of methylaminopropylamine, methylaminoethylamine, butylaminopropylamine, butylaminoethylamine, octylaminopropylamine, octylaminoethylamine, dodecylaminopropylamine, dodecylaminoethylamine, hexadecylaminopropylamine, hexadecylaminoethylamine, octadecylaminopropylamine, octadecylaminoethylamine, isopropyloxypropyl-1,3-diaminopropane, octyloxypropyl-1,3-diaminopropane and mono-alkylated alkylene damines derived from fatty acids.

31. The process of claim 30 wherein said mono-alkylated alkylene diamine comprises at least one member selected from the group consisting of N-coco alkyl-1,3-propanediamine, N-tallow alkyl-1,3-propanediamine and N-oleyl-1,3-propanediamine.

32. The process of claim 23, wherein the molybdenum source comprises at least one member selected from the group consisting of ammonium molybdate, sodium molybdate and molybdenum oxides.

33. The process of claim 23, wherein the molybdenum source (component iii) is present in an amount of from 0.5 to 1.5 moles per mole of fatty oil (component i).

34. The process of claim 23, wherein components (i) and (ii) are reacted to form a reaction mixture prior to the addition of components (iii) and (iv).

* * * * *